United States Patent [19]

Halpern

[11] 4,154,930

[45] May 15, 1979

[54] PENTATE SALTS OF AMINO-S-TRIAZINES

[75] Inventor: Yuval Halpern, Skokie, Ill.

[73] Assignee: Borg-Warner Corporation, Chicago, Ill.

[21] Appl. No.: 937,341

[22] Filed: Aug. 28, 1978

[51] Int. Cl.[2] .................. C07D 251/70; C07D 251/52; C07D 251/46

[52] U.S. Cl. ..................................... 544/195; 252/8.1; 260/45.8 NT; 260/45.8 NE; 512/70; 512/143

[58] Field of Search ......................................... 544/195

[56] References Cited

U.S. PATENT DOCUMENTS 3,876,635   4/1975   Deiner et al. ........................ 544/195

Primary Examiner—John M. Ford
Attorney, Agent, or Firm—Richard J. Schlott

[57] ABSTRACT

Pentate salts of amino-s-triazines having the formula

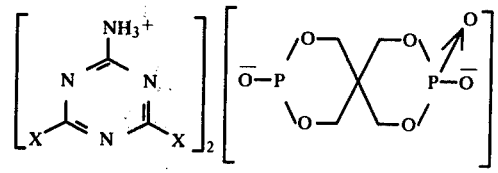

wherein x is -NH$_2$ or -OH are useful as flame retardants and foaming agents for polymers.

9 Claims, No Drawings

PENTATE SALTS OF AMINO-S-TRIAZINES

BACKGROUND OF THE INVENTION

Amino-s-triazines of the formula

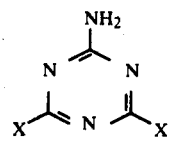

wherein x may be —$NH_2$ or —OH, are known in the art, as are many derivatives thereof. The chemistry of melamine (x=$NH_2$), and ammelide (x=OH) is summarized in "s-Triazines and Derivatives", Interscience Publishers, Inc., New York, 1959.

Spiro phosphate compounds of the structure

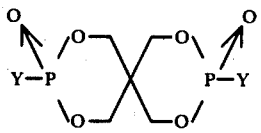

wherein Y is —OR or —Cl, are also known in the art, and are referred to as derivatives of pentaerythritol diphosphates or by the coined term pentates; e.g., where Y=Cl, the compound may be called dichloropentate. Salts of the free acid, wherein Y is —OH, do not appear to be widely studied.

SUMMARY OF THE INVENTION

Amino-s-triazines react with the hydrolysis product of dichloropentate to form water-insoluble or sparingly soluble salts having the structure

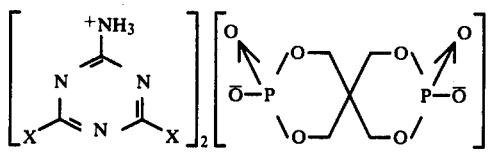

wherein x is selected from the group consisting of —$NH_2$ and —OH.

The compounds of the instant invention are new compositions of matter, and find use in the plastics formulating arts as blowing agents, char-forming additives and the like.

DESCRIPTION OF THE PREFERRED EMBODIMENTS

The pentate salts of amino-s-triazines are readily prepared by first hydrolyzing a pentate compound such as dichloropentate to provide the free acid, then reacting that product with the requisite amount of the amino-s-triazine to form the sparingly soluble salt. In one embodiment, the dichloropentate is first hydrolyzed by warming with aqueous alkali. This product is then added to a warm (70°–100° C.) aqueous solution of the amino-s-triazine containing sufficient mineral acid to dissolve the triazine. The sparingly soluable pentate salt precipitates from solution as a fine powder or crystalline material. As an alternative embodiment, an acid acceptor such as a tertiary amine may be employed in place of the alkali to promote the hydrolysis reaction. As a third alternative embodiment, the amino-s-triazine may be added to the aqueous mixture prior to hydrolysis, whereupon the pentate salt is formed and precipitates as the hydrolysis proceeds.

The following examples are provided by way of illustration, but are by no means exhaustive of the various approaches that may be employed to prepare the compounds of this invention.

EXAMPLE I. PREPARATION OF MELAMMONIUM PENTATE

Into a 100 ml round bottom flask were added 0.01 M (2.97 g) of dichloropentate, 0.02 M (2.52 g) of melamine, and 25 ml of water. The mixture was stirred and heated under reflux for 15 min., then cooled first to room temperature, then with an ice bath. The powdery precipitate was isolated by filtering. The precipitate was washed with cold water, then dried en vacuo at 50°–100° C. to a constant weight, providing 4.23 g or a white powder (82% yield). The product was identified by I.R., elemental analysis and $^{13}C$ NMR as melammonium pentate, $C_{11}H_{22}O_8P_2$, having the structure.

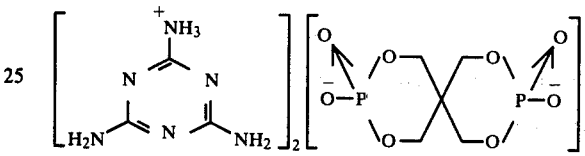

Thermogravametric analysis was carried out in air at a temperature rise of 20° C./min. Melammonium pentate decomposed sharply beginning at 290° C. (540° F.) to gaseous products. When placed in a burner flame, melammonium pentate decomposed without burning to form a foamed char. The char, further exposed to flame, did not burn.

EXAMPLE 2. PREPARATION OF THE PENTATE SALT OF AMMELIDE

The procedure of Example 1 was followed, employing 0.02 M of ammelide in place of melamine. A fine white powder was obtained which was identified by I.R. and elemental analysis as the pentate salt of ammelide, $C_{11}H_{20}N_{10}O_{10}P_2$, having the structure

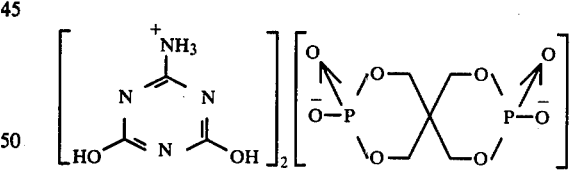

Thermogravametric analysis in air at a temperature rise of 20° C./min showed that the pentate salt of ammelide decomposed sharply beginning at 290° C. (540° F.) to give gaseous products. When placed in a burner flame, the pentate salt of ammelide decomposed without burning to form a foamed char. The char, further exposed to flame, did not burn.

The compounds of this invention are thus useful as gas-forming agents for foaming of plastics and as char-forming additives. In further tests, melammonium pentate, Example 1, was compounded with polypropylene by mixing 100 parts of powdered polypropylene with 30 parts of melammonium pentate. The mixture was compression molded at a platen temperature of 420° F. to give a white, ⅛" thick plaque. Strips cut from this plaque were tested for flammability by holding vertically in the flame of a Meeker burner for ten seconds, then removing the flame source. The specimens were coated with a char, and were self extinguishing, non-burning and non-dripping. The pentate salts of this invention are thus sufficiently stable to permit compounding and thermal processing in conventional equipment. When heated to temperatures substantially greater than 500° F., compositions containing the pentate salts of this invention expand due to thermal decomposition of the pentate salt and produce foam structures.

It will thus be apparent that the pentate salts of amino-s-triazines selected from the group consisting of melamine and ammelide possess unexpected properties useful in the production of flame retardant compositions and foamed plastic structures.

I claim:

1. Pentate salts of amino-s-triazines of the following structure

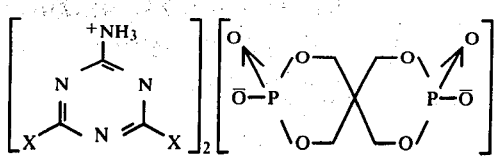

wherein x is selected from the group consisting of —NH$_2$ and —OH.

2. Melammonium pentate.
3. The pentate salt of ammelide.
4. A method for preparing pentate salts of amino-s-triazines comprising hydrolyzing dihalopentate, reacting the hydrolysis product with an amino-s-triazine, and isolating the salt.
5. The method of claim 4 wherein the amino-s-triazine is selected from the group consisting of melamine and ammelide.
6. The method of claim 4 wherein the step of hydrolyzing dihalopentate is carried out with aqueous alkali.
7. The method of claim 4 wherein the step of hydrolyzing dihalopentate is carried out in water in the presence of the amino-s-triazine.
8. The method of claim 4 wherein the step of hydrolyzing dihalopentate is carried out in water in the presence of a tertiary amine.
9. The substantially water-insoluble product produced by heating under reflux condiditons a mixture of an amino-s-triazine and a dihalopentate in the molar ratio of about 2:1 in the presence of water.